(12) United States Patent
Arts

(10) Patent No.: US 8,226,642 B2
(45) Date of Patent: Jul. 24, 2012

(54) SURGICAL GAS PLASMA IGNITION APPARATUS AND METHOD

(75) Inventor: Gene H. Arts, Berhoud, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 914 days.

(21) Appl. No.: 12/191,799

(22) Filed: Aug. 14, 2008

(65) Prior Publication Data

US 2010/0042094 A1 Feb. 18, 2010

(51) Int. Cl.
*A61B 18/04* (2006.01)
(52) U.S. Cl. .......................................... 606/41
(58) Field of Classification Search ............ 606/27, 606/32, 34, 41, 42
See application file for complete search history.

(56) References Cited

U.S. PATENT DOCUMENTS

| | | | |
|---|---|---|---|
| 2,708,933 A | 5/1955 | August | |
| 2,828,747 A | 4/1958 | August | |
| 3,434,476 A | 3/1969 | Shaw et al. | |
| 3,569,661 A | 3/1971 | Ebeling | |
| 3,595,239 A | 7/1971 | Petersen | |
| 3,692,973 A | 9/1972 | Oku et al. | |
| 3,699,967 A | 10/1972 | Anderson | |
| 3,832,513 A | 8/1974 | Klasson | |
| 3,838,242 A | 9/1974 | Goucher | |
| 3,903,891 A | 9/1975 | Brayshaw | |
| 3,970,088 A | 7/1976 | Morrison | |
| 3,987,795 A | 10/1976 | Morrison | |
| 4,014,343 A | 3/1977 | Esty | |
| 4,019,925 A | 4/1977 | Nenno et al. | |
| 4,040,426 A | 8/1977 | Morrison, Jr. | |
| 4,041,952 A | 8/1977 | Morrison, Jr. et al. | |
| 4,043,342 A | 8/1977 | Morrison, Jr. | |
| 4,057,064 A | 11/1977 | Morrison, Jr. et al. | |
| 4,060,088 A | 11/1977 | Morrison, Jr. et al. | |
| 4,209,018 A | 6/1980 | Meinke et al. | |
| 4,242,562 A | 12/1980 | Karinsky et al. | |
| 4,311,145 A | 1/1982 | Esty et al. | |
| 4,492,231 A | 1/1985 | Auth | |
| 4,492,845 A | 1/1985 | Kljuchko et al. | |
| 4,545,375 A | 10/1985 | Cline | |

(Continued)

FOREIGN PATENT DOCUMENTS

DE 3710489 11/1987

(Continued)

OTHER PUBLICATIONS

Grund et al., "Endoscopic Argon Plasma . . . Flexible Endoscopy"; Endoscopic Surgery and Allied Technologies, No. 1, vol. 2, pp. 42-46 (Feb. 1994).

(Continued)

*Primary Examiner* — Christopher D Koharski

(57) ABSTRACT

Disclosed is an ignition system for initiating a plasma arc in an electrosurgical system. The system includes a source of high frequency electrical energy having a terminal of active potential and a terminal of return potential a base having a distal end from which a plasma arc emanates, an active electrode operatively coupled with the base and electrically in circuit with the terminal of active potential. The ignition system may have a piezoelectric device electrically coupled to the active electrode to create at least one high voltage spark when the system is initially activated. Alternately, the ignition system may include a heater or heating device of heating the active electrode and producing free electrons to assist in the initiation of the plasma arc.

15 Claims, 5 Drawing Sheets

U.S. PATENT DOCUMENTS

| | | |
|---|---|---|
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmanesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Black et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanion et al. |
| 5,697,882 A | 12/1997 | Eggers et al. |
| 5,700,260 A | 12/1997 | Cho et al. |
| 5,716,365 A | 2/1998 | Goicoechea et al. |
| 5,720,745 A | 2/1998 | Farin et al. |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,149,648 A | 11/2000 | Cosmescu |
| 6,197,026 B1 | 3/2001 | Farin et al. |
| 6,213,999 B1 * | 4/2001 | Platt et al. .................. 606/27 |
| 6,264,650 B1 | 7/2001 | Hovda et al. |
| 6,475,217 B1 | 11/2002 | Platt |
| 6,558,383 B2 | 5/2003 | Cunningham et al. |
| 6,602,249 B1 | 8/2003 | Stoddard |
| 6,616,660 B1 | 9/2003 | Platt |
| 6,632,193 B1 * | 10/2003 | Davison et al. .................. 604/22 |
| 6,666,865 B2 | 12/2003 | Platt |
| 6,852,112 B2 | 2/2005 | Platt |
| 6,911,029 B2 | 6/2005 | Platt |
| 7,033,353 B2 | 4/2006 | Stoddard |
| 2002/0022838 A1 | 2/2002 | Cunningham et al. |
| 2003/0093073 A1 | 5/2003 | Platt |
| 2003/0125727 A1 | 7/2003 | Truckai et al. |
| 2003/0144654 A1 | 7/2003 | Hilal |
| 2004/0167512 A1 | 8/2004 | Stoddard |
| 2004/0167617 A1 | 8/2004 | Voellmicke et al. |
| 2005/0015086 A1 | 1/2005 | Platt |
| 2005/0070894 A1 | 3/2005 | McClurken |
| 2005/0171528 A1 | 8/2005 | Sartor |
| 2005/0187542 A1 * | 8/2005 | Auge et al. .................. 606/32 |
| 2005/0197658 A1 | 9/2005 | Platt |
| 2006/0052771 A1 | 3/2006 | Sartor |
| 2006/0052772 A1 | 3/2006 | Sartor et al. |
| 2006/0200122 A1 | 9/2006 | Sartor et al. |
| 2007/0120482 A1 * | 5/2007 | Michael et al. .................. 313/568 |
| 2007/0208337 A1 | 9/2007 | Podhajsky et al. |
| 2007/0213709 A1 | 9/2007 | Podhajsky |

FOREIGN PATENT DOCUMENTS

| | | |
|---|---|---|
| DE | 4139029 | 6/1993 |
| DE | 4326037 | 2/1995 |
| DE | 9117019 | 4/1995 |
| DE | 19537897 | 3/1997 |
| DE | 9117299 | 4/2000 |
| DE | 19848784 | 5/2000 |
| DE | 29724247 | 8/2000 |
| EP | 0 447 121 A2 | 9/1991 |
| EP | 0 612 535 A1 | 8/1994 |
| EP | 0956827 A1 | 11/1999 |
| EP | 1 090 599 A1 | 4/2001 |
| EP | 1 127 551 A1 | 8/2001 |
| EP | 1 199 037 A2 | 4/2002 |
| EP | 1 199 038 A2 | 4/2002 |
| EP | 1 199 037 A3 | 7/2003 |
| EP | 1 199 038 A3 | 7/2003 |
| EP | 1 323 384 A2 | 7/2003 |
| EP | 1 323 384 A3 | 1/2004 |
| EP | 1 561 430 A1 | 8/2005 |
| EP | 1561430 | 8/2005 |
| EP | 1 570 798 A2 | 9/2005 |
| EP | 1 595 507 A2 | 11/2005 |
| FR | 1340509 | 9/1963 |
| GB | 1014995 | 12/1965 |
| JP | 61-159953 | 7/1986 |
| SU | 1438745 | 11/1988 |
| WO | WO 91/13593 | 9/1991 |
| WO | WO 93/03678 | 3/1993 |
| WO | WO 96/24301 | 8/1996 |
| WO | WO 96/27337 | 9/1996 |
| WO | WO 99/15091 | 4/1999 |
| WO | WO 01/62333 | 8/2001 |
| WO | WO 02/058762 A2 | 8/2002 |
| WO | WO 02/058762 A3 | 8/2002 |
| WO | WO 2005/016142 | 2/2005 |

OTHER PUBLICATIONS

Farin et al., Technology of Argon Plasma . . . Endoscopic Applications; Endoscopic Surgery and Allied Technologies, No. 1, vol. 2, pp. 71-77 (Feb. 1994).

Brand et al., "Electrosurgical Debulking of Ovarian Cancer: A New Technique Using the Argon Beam Coagulator"; Gynecologic Oncology 39 pp. 115-118 (1990).

Hernandez et al., "A Controlled Study of the Argon Beam Coagultor for Partial Nephrectomy"; The Journal of Urology, vol. 143, May (J. Urol. 143: pp. 1062-1065, 1990).

Ward et al., "A Significant New Contribution to Radical Head and Neck Surgery"; Arch Otolaryngology, Head and Neck Surg., vol. 115 pp. 921-923 (Aug. 1989).

Mark H. Mellow, "The Role of Endoscopic Laser Therapy in Gastrointestinal Neoplasms"; Advanced Therapeutic Endoscopy, pp. 17-21, 1990.

Silverstein et al., "Thermal Coagulation Therapy for Upper Gatrointestinal Bleeding"; Advanced Therapeutic Endoscopy, pp. 79-84, 1990.

Waye et al., "Endoscopic Treatment Options"; Techniques in Therapeutic Endoscopy, pp. 1.7-1.15, 1987.

European Search Report EP 01 10 2843.8-2305, dated May 15, 2001.

International Search Report PCT/US98/19284, dated Jan. 14, 1999.

European Search Report EP 05 00 2257, dated Jun. 1, 2005.

European Search Report EP 06 01 9572 dated Nov. 21, 2006.

European search Report 07 00 4356.

Written Opinion and European Search Report from counterpart European Application No. 09010519 dated Nov. 16, 2009.

* cited by examiner

SURGICAL GAS PLASMA IGNITION APPARATUS AND METHOD

BACKGROUND

1. Technical Field

This present disclosure relates to surgical devices which incorporate electro-surgical energy and gas plasmas. More specifically, the present disclosure relates to an improved apparatus and method for igniting the plasma.

2. Background of Related Aft

Surgical devices using gas plasma to conduct electrosurgical energy to a patient are well known in the art, as are techniques for igniting the gas plasma, and creating a plasma arc. Several of these techniques require creating a sufficiently strong electrical field that can ignite the plasma. One such technique is to move the tip of an electrode very close to the surgical site. The electric field along a path between the electrode and the surgical site increases as the separation between the electrode and the surgical site decreases. The electric field created between the electrode and the surgical site reaches a level sufficient to ignite the plasma. Another technique for igniting the gas plasma is to use a pointed electrode which generates a stronger electrical field at the tip, assisting in plasma ignition.

In yet another technique, a corona or corona discharge is created to ignite the plasma. As disclosed in U.S. Pat. No. 6,213,999, the entire disclosure of which is herein incorporated by reference, creating a corona discharge is achieved using a corona return electrode. The corona return electrode is located on the surgical handpiece and is electrically connected to the return potential of the electrosurgical generator. The corona return electrode is physically distinct from the electrosurgical return electrode although they are both electrically in circuit with the return potential of the electrosurgical generator. A dielectric barrier is required to prevent arcing between the active electrode and the corona return electrode. The dielectric barrier may also be used to prevent arcing between the ionized gas and the corona return electrode. A non-uniform electric field is generated between the corona return electrode and the active electrode. If sufficiently strong, this electric field causes a corona to form around the active electrode. The corona subsequently aids in the ignition of the plasma arc.

In each of the aforementioned techniques, a sufficiently strong electric field is necessary to ignite the gas. Once the gas is ignited and a plasma arc is formed a weaker electric field may maintain the plasma arc.

SUMMARY

Provided is an ignition system for initiating a plasma arc in an electrosurgical system. The system comprises a source of high frequency electrical energy having a terminal of active potential and a terminal of return potential, a base having a distal end from which the plasma arc emanates, an active electrode operatively coupled with the base and electrically in circuit with the terminal of active potential, and a piezoelectric device electrically coupled to the active electrode to create at least one high voltage spark when the system is initially activated.

The ignition system may further include a corona return electrode operably coupled to the base and electrically in circuit with the terminal of return potential, the corona return electrode coupled to the active electrode adjacent to the distal end of the base to form a corona discharge adjacent the distal end of the base member. The ignition system may further include a dielectric member disposed between the active electrode and the corona return electrode.

The ignition system may also include a heater configured to preheat the active electrode prior to activation. The heater may utilize a current source selected from at least one of a DC current, AC current and RF current to preheat the active electrode prior to activation. The current source may be provided by the source of high frequency electrical energy. The current source may also be provided by an independent current source. The ignition system may also include a current sensor.

The piezoelectric device includes a striking mechanism. The striking mechanism may continuously activate until a current sensor senses a current, whereupon a source of electrosurgical current maintains a normal current.

Further provided is a method of using a plasma ignition system for initiating a plasma arc in an electrical system. The method comprising the steps of providing an electrosurgical device comprising, a source of high frequency electrical energy having a terminal of active potential and a terminal of return potential, a base having a distal end from which the plasma arc emanates, an active electrode operatively coupled with the base and electrically in circuit with the terminal of active potential, and a piezoelectric device electrically coupled to the active electrode to create at least one initial high voltage spark when the system is initially activated, energizing the active electrode and actuating the piezoelectric device to create an increased voltage near the distal end of the holder thereby initiating a plasma arc. The electrosurgical device may further includes a corona return electrode operably coupled to the base and electrically in circuit with the terminal of return potential. The method may further include the step of actuating the corona return electrode to assist in initiating the plasma arc.

The electrosurgical device may further include a heater configured to preheat the active electrode prior to activation. The method further including the step of activating the heater.

BRIEF DESCRIPTION OF THE DRAWINGS

The foregoing summary, as well as the following detailed description will be better understood when read in conjunction with the appended figures. For the purpose of illustrating the present disclosure, one particular embodiment is shown. It is understood, however, that the present disclosure is not limited to the precise arrangement and instrumentalities shown.

DETAILED DESCRIPTION

Figure 1:
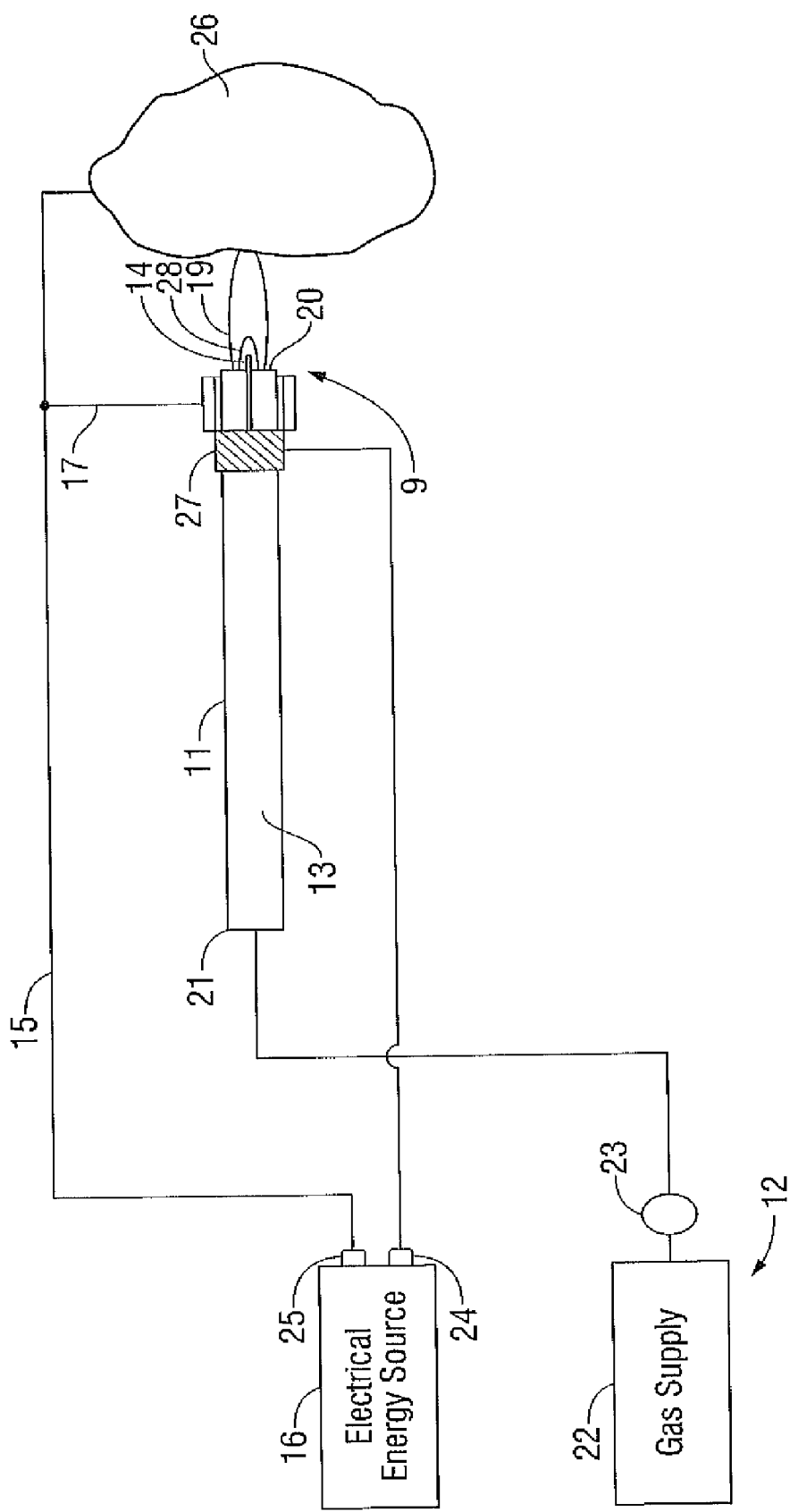
FIG. 1 is a schematic diagram of a monopolar electrosurgical system with a source of regulated gas and a gas plasma ignition apparatus in accordance with the present disclosure.

Particular embodiments of the plasma ignition apparatus in accordance with the present disclosure will now be described in detail with reference to the drawing figures wherein like reference numerals identify similar or identical structural elements. As shown in the drawings and described throughout the following description, as is traditional when referring to relative positioning on an object, the term "proximal" refers to the end of the apparatus which is closer to the user and the term "distal" refers to the end of the apparatus which is further from the user.

A primary basis of the ignition apparatus is the formation of a corona, which is a type of plasma discharge that is distinct from the plasma arc. A corona return electrode is used in connection with an active electrode to create a non-uniform electric field that is conducive to the formation of a corona. As described above, the corona then assists in igniting the plasma arc.

One envisioned embodiment of the plasma ignition system 10 is shown in FIG. 1 which may be used in electrosurgical systems that have a regulated source of ionizable gas 12. Plasma ignition system 10 includes a handpiece or base 11 having a passage 13 defined therethrough for the passage of gas. The system 10 also includes a regulated source of ionizable gas 12, an active electrode 14, an electrical return 15, a source of high frequency electrical energy 16, and corona start feature 9.

Handpiece 11 is configured to allow a surgeon to control application of a plasma arc 19. Handpiece 11 may have a knurled or ergonomically formed surface for ease of handling. In the present embodiment, handpiece 11 is generally pencil-like and includes an elongated tubular body. Other structures are also envisioned and have been contemplated, including handpieces designed for use with endoscopic and laparoscopic surgeries. Handpiece 11 includes a distal end 20 and a proximal end 21. Distal and proximal ends 20, 21, respectively, are disposed in fluid communication with passage 13. More particularly, proximal end 21 of handpiece 11 is configured to receive an ionizable gas from gas supply 12 and distal end 20 is configured to emit the ionizable gas supplied from gas supply 12.

The regulated source of ionizable 12 is typically a pressure vessel 22, with a gas regulator 23 attached thereto. The ionizable gas is typically argon, although other gases, particularly the noble gases, are known to be ionizable and may be used. Passage 13 defined through handpiece 11 is connected at the proximal end 21 to the regulated source of ionizable gas 12 such that the gas can flow through handpiece 11 and out distal end 20.

The source of high frequency electrical energy 16 is typically an electrosurgical generator, for example, electrosurgical generators sold by VALLEYLAB—a division of TYCO Healthcare LP in Boulder, Colo. Electrosurgical generators output currents having various waveforms and frequencies depending on the intended use or application. For example, output currents vary for such applications as fulguration, desiccation, and coagulation.

Electrosurgical generator 16 includes electrical terminals 24, 25 of active and return potentials, respectively. Active electrode 14 is electrically connected to the active terminal 24 on electrosurgical generator 16 and is generally located at the distal end of passage 13 such that the ionizable gas flowing through handpiece 11 comes into contact with and passes by active electrode 14.

Figure 4:
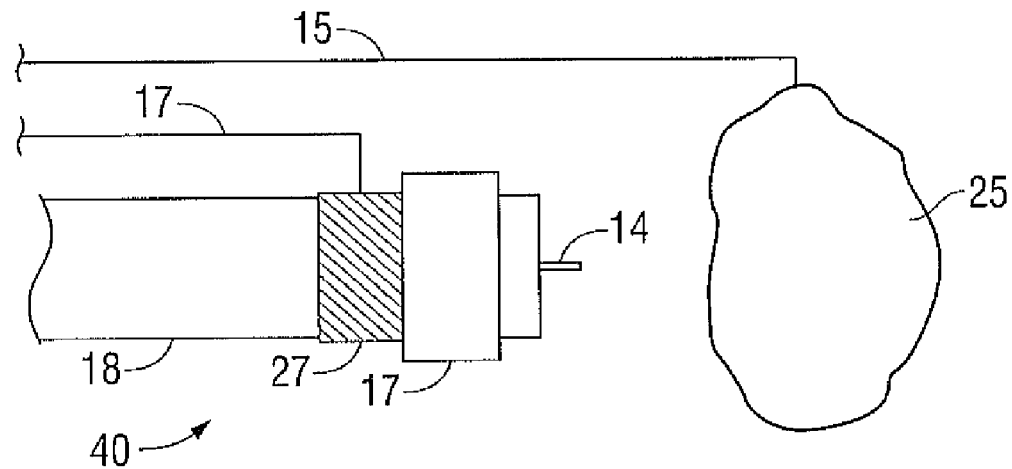
FIG. 4 is a schematic diagram showing the distal end of a handpiece for an alternate embodiment of a monopolar electrosurgical.

An electrical return path 15 is connected to the source of high frequency electrical energy 16, and is also in circuit with the tissue or bodily fluids of the patient 26. Electrical return 15 may be attached separately to the patient 26 in a monopolar system 40, as shown in FIG. 4. Alternately, electrical return 15 may be on handpiece 11 in a bipolar or sesquipolar system 50, as shown in FIG. 5.

Figure 5:
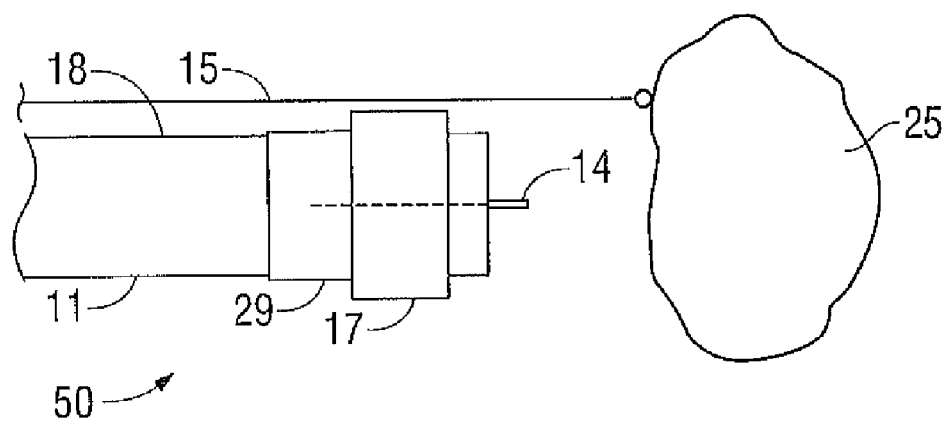
FIG. 5 is a schematic diagram showing the distal end of a handpiece for a bipolar electrosurgical system.

Corona start feature 9 includes a corona return electrode 17 and a dielectric member 18 (See FIGS. 4 and 5). Corona return electrode 17 is typically located near distal end 20 of handpiece 11. Corona return electrode 17 is electrically connected to return path 15 of the electrosurgical generator 16. The function of corona return electrode 17 is to establish a non-uniform electrical field with active electrode 14. The non-uniform electric field causes the formation of a corona 28 near active electrode 14, which will thereby aid in the initiation of a surgical plasma arc 19.

Dielectric member 18 separates active electrode 14 from corona return electrode 17. The resulting electrical coupling between active electrode 14 and corona return electrode 17 is substantially capacitive in nature. The electrical coupling between active electrode 14 and corona return electrode 17 causes an electrical current to develop in the corona return electrode 17. The current is typically small compared with the amount of current in electrical return 15 when a circuit has been closed through patient 26. Dielectric member 18 may be constructed from a ceramic or other insulative material and is preferably electrically "leaky", which permits the creation of an electric field more conducive to creating a corona and initiating a plasma arc 19.

Figure 2:
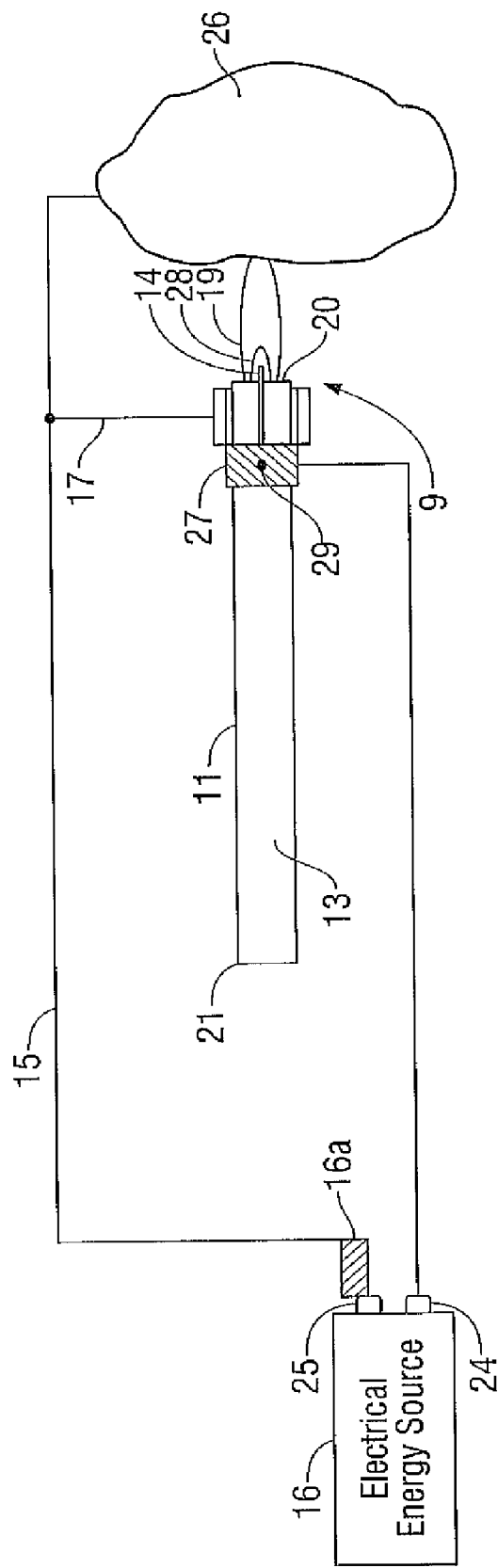
FIG. 2 is a schematic diagram of a monopolar electrosurgical system with the gas plasma ignition apparatus of FIG. 1.
Figure 3:
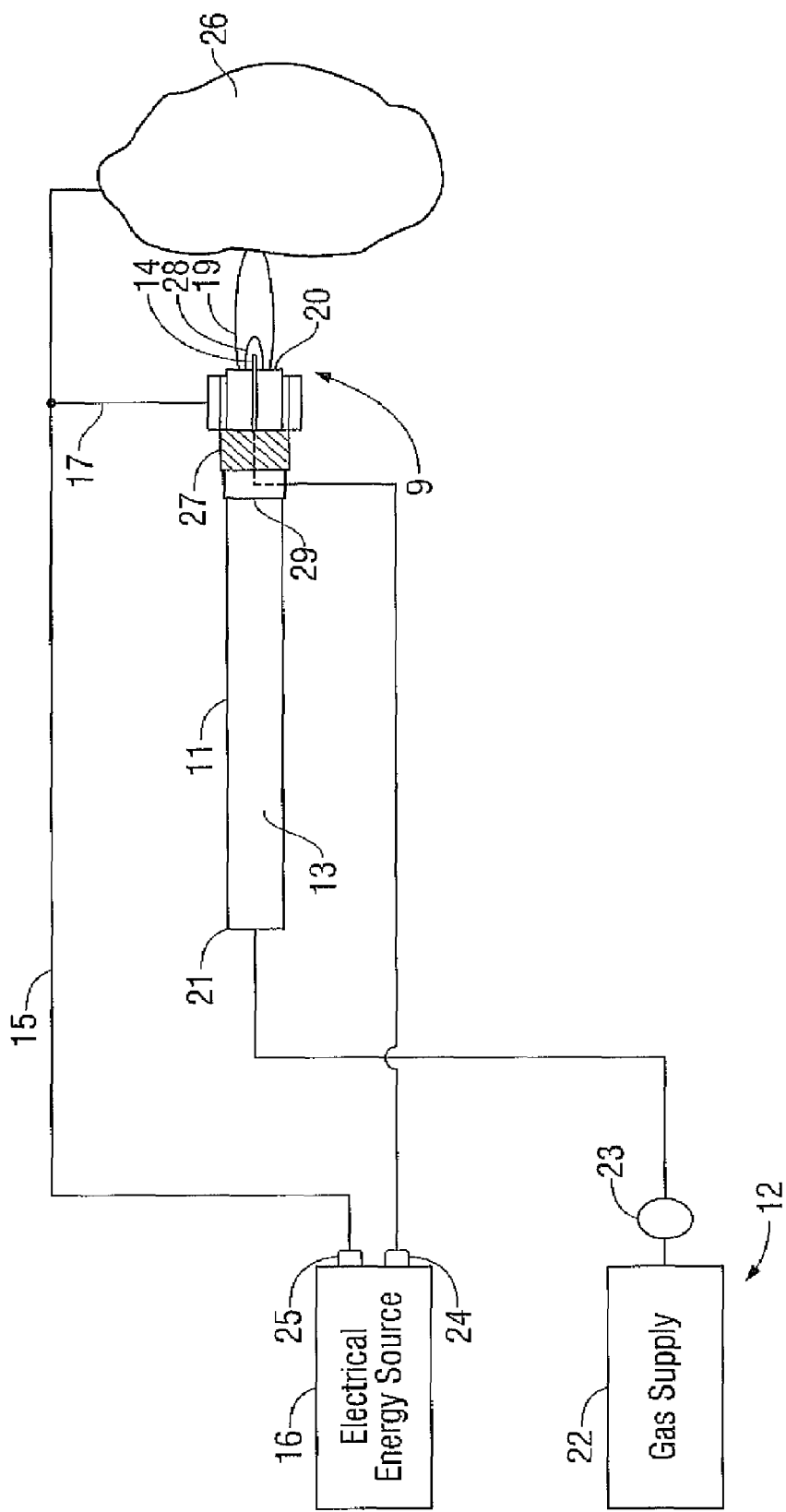
FIG. 3 is a schematic diagram of a monopolar electrosurgical system with a source of regulated gas and an alternate embodiment of a gas plasma ignition apparatus.

Another embodiment of plasma ignition system 10, as shown in FIG. 2, can be used with an electrosurgical system 30 that does not have a regulated supply of ionizable gas. These systems are required to ionize air in the region between active electrode 14 and patient 25 in order to conduct electrosurgical energy to patient 25 without physical contact of active electrode 14. This embodiment includes a handpiece 11, an active electrode 14, an electrical return 15, a source of high frequency electrical energy 16, and a corona start feature 9. As described above, corona start feature 9 includes a corona return electrode 17 and a dielectric member 18. This embodiment is designed to generate a non-uniform electric field between active electrode 14 and corona return electrode 17 so that a corona 28 forms near active electrode 14. Corona 28 will then aid in the ionization of the air gap between active electrode 14 and patient 25.

Several embodiments of corona return electrode 17 have been contemplated. The desired objective is the production of a non-uniform electric field that has sufficient strength to generate corona 28. In one embodiment, corona return electrode 17 is a conductive mesh which is disposed over the outer surface of dielectric member 18. In another embodiment, as shown in FIG. 4, dielectric member 18 is a tube, and corona return electrode 17 is a conductive deposit on the outer surface of dielectric member 18. In yet another embodiment, corona return electrode 17 is a conductive mesh embedded in dielectric member 18. As described above, dielectric member 18 may be electrically leaky. Manipulation of the size, shape, and placement of the electrodes 14, 17 and dielectric member 18 can produce the desired field characteristics.

Modifications may also be made to electrosurgical generator 16 to increase the reliability and effectiveness of corona start feature 9. For example, generator 16 may be configured to generate a higher voltage output when plasma ignition system 10 is first keyed. The repetition frequency or duty cycle of the output may be reduced during this initial period to minimize high frequency leakage. The output reduction may be limited to a number of cycles or a period of time. Once the predetermined number of cycles have occurred or the period of time has elapsed, the generator output may return to normal output frequency and voltage.

Generator 16 may include a plasma ignition system 10 having a current sensor 16a which controls the high voltage and/or frequency or duty cycle output of generator 16. Once the current sensor 16a senses a current in return electrode 15, or in other words, once plasma arc 19 has been initiated, electrosurgical generator 16 may resume a normal frequency and voltage output. The current sensor 16a may be mounted on generator 16, on handpiece 11 or anywhere therebetween where the closed circuit can be detected. The modifications to electrosurgical generator 16 may be adaptable to both electrosurgical systems utilizing ionizable gas and those systems that do not use ionizable gas.

Independent of, or in addition to the corona start feature and/or modified generator, plasma ignition system 10 may further include a piezoelectric device 27 for assisting in creating plasma arc 19. Piezoelectric device 27 incorporates piezoelectric crystals to generate a voltage in response to a mechanical stress. Piezoelectric crystals are well known, as are their physical properties and applications. It is envisioned that all piezoelectric crystals and other like materials, capable of generating a voltage in response to a mechanical stress, may be used in piezoelectric device 27. Although reference may be made to a single crystal, multiple crystals of the same or different materials may be included in piezoelectric device 27.

Piezoelectric device 27 is electrically connected between active potential 24 of electrosurgical generator 16 and active electrode 14. Piezoelectric device 27 may be positioned on, about, or within handpiece 11. Piezoelectric device 27 may take any form, including a box configured to mount on handpiece 11 or a tube capable of being positioned about handpiece 11. Piezoelectric device 27 may also be mounted on electrosurgical generator 16. It is further envisioned that piezoelectric device 27 may be remotely connected between active potential 24 and active electrode 14.

Piezoelectric device 27 is configured to create a high voltage spark when plasma ignition system 10 is first keyed. In addition to initiating gas and current flow, the initial keying of plasma ignition system 10 actuates a striking mechanism 29 within piezoelectric device 27 which strikes the piezoelectric crystal. The striking of the crystal generates a high voltage between active electrode 14 and patient 26. The striking mechanism 29 may be mechanically or electrically actuated by a button, switch or the like, mounted on handpiece 11 or electrical generator 16. The button, switch or the like may also be positioned remotely, for example, on a foot pedal connected to either handpiece 11, electrosurgical generator 16, or both.

Although piezoelectric device 27 may operate to ignite plasma arc 19 upon the initial strike of the piezoelectric crystal, repeated strikes may be necessary to achieve plasma ignition. In one embodiment, the striking mechanism 29 may be continuously actuated until a sensing mechanism (which may be the same as sensor 16a or an additional sensor disposed on or in the system 10), either in handpiece 11 or electrosurgical generator 16, detects plasma arc 19. The sensing mechanism may work in conjunction with the modified electrosurgical generator 16, described above, to keep the striking mechanism actuated until plasma arc 19 has been initiated. Both the electrosurgical generator 16 and piezoelectric device 27 may operate to produce an increase voltage until the sensing mechanisms (or sensor 16a) sense plasma arc 19, thus deactivating piezoelectric device 27 and switching electrosurgical generator 16 to normal frequency and voltage outputs. In another embodiment, the striking mechanism 29 may be continuously actuated until the user recognizes plasma arc 19 has been initiated and manually deactivates the striking mechanism 29. It is further envisioned that a delayed actuation of the striking mechanism 29, beyond plasma ignition system 10 first being keyed, may also be desired.

The resulting high voltage generates an electric current between active electrode 14 and patient 26 sufficiently strong to initiate plasma arc 19. Once initiated, plasma arc 19 is maintained with normal generator voltage provided by electrosurgical generator 16. Plasma arc 19 may be initiated solely from the high voltage generated by piezoelectric device 27 or in combination with any of the other presently disclosed methods.

Independent of, or in addition to, corona start feature 9, modified electrosurgical generator 16, and/or piezoelectric device 27, plasma ignition apparatus 10 may further include a heater 28 for preheating active electrode 14 prior to the initial keying of plasma ignition apparatus 10. The preheating of active electrode 14 causes the release of many free electrons. The free electrons improve arc initiation by reducing the resistance between active electrode 14 and patient 26. Heater 28 may be configured to mount on or about handpiece 11. Heater 28 my utilize DC current, AC current or RF current to preheat active electrode 14. The additional current may be provided directly by electrosurgical generator 16. It is also envisioned that heater 28 could have an independent and/or remote source of DC, AC, or RF current. As with the previously disclosed apparatuses and methods for assisting in the ignition of a plasma arc, heater 28 may be adaptable for use with electrosurgical systems utilizing ionizable gas and systems that do not utilize gas.

Figure 6:
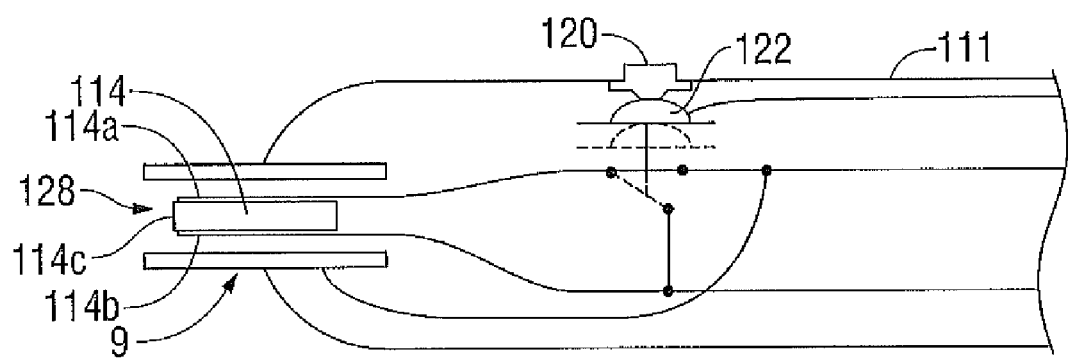
FIG. 6 is a schematic diagram showing the distal end of a handpiece including a heater.

Turning now to FIG. 6, a detailed embodiment of handpiece 111, including a heating mechanism 128, is shown. As discussed above, with respect to heater 28, heating mechanism 128 operates to heat active electrode 114 which results in the release of electrons therefrom to aid in the initiation of a plasma arc. As shown, electrode 114 includes of a pair of metal wires 114a, 114b, e.g., tungsten or other suitable metal, separated at the tip by ceramic insulator 114c. Handpiece 111 includes an activation button 120 configured to engage a dome switch 122.

Initially, activation button 120, and therefore, dome switch 122 are in an "off" position. Depression of activation button 120 to a first position causes dome switch 122 into a first position and may also activate the flow of gas through handpiece 111. In this first position, a circuit is completed across ceramic insulator 114c causing ceramic insulator 114c to heat up and become hot. Further depression of activation button 120 further depresses dome switch 122, thereby causing the disconnection of the circuit across ceramic insulator 114c and the connection both wires 114a, 114b of active electrode 114 with the source of electrosurgical energy (not shown). Once the connection is completed the plasma arc initiates. As discussed above with relation to heater 28, a heater 128 may be used separately or in conjunction with a corona start feature 9.

Figure 7:
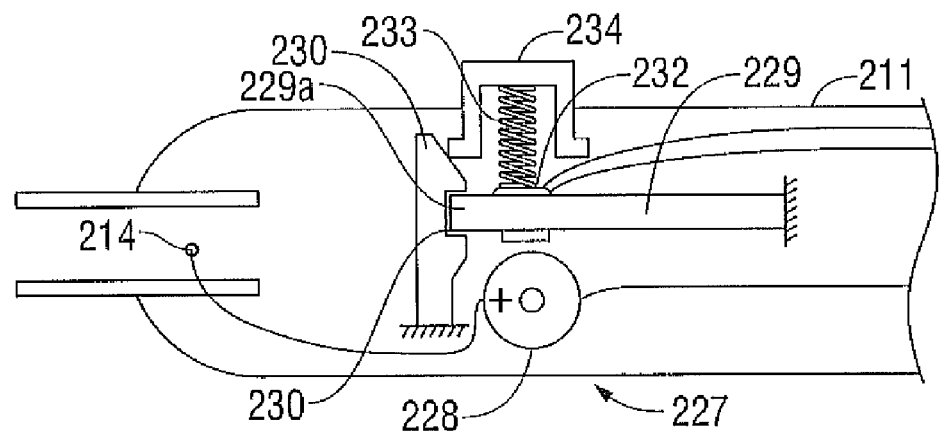
FIG. 7 is a schematic diagram showing distal end of a handpiece including a piezoelectric device.

Turning now to FIG. 7, a detailed embodiment of handpiece 211, including a piezoelectric device 227, is shown. Piezoelectric device 227 includes a piezoelectric crystal 228, a striking member or hammer 229, and a catch/release lever 230. Piezoelectric crystal 228 is of a type capable of producing a voltage spike when struck. Piezoelectric crystal 228 is connected in series with an active electrode 214. In the present embodiment, hammer 229 is in the form of a cantilevered beam, however, it is envisioned that a striking mechanism of any manner may be used to strike piezoelectric crystal 228. Mounted on a distal end 229b of hammer 229 is a dome switch 232. Dome switch 232 is configured to key gas flow and electrosurgical energy upon depression of an activation button 234. Disposed between actuation button 234 and dome switch 232 is a spring 233. When compressed, spring 233 is configured to exert a force on distal end 229b of hammer 229.

In an initial, inactivated condition, distal end 229b of hammer 229 is received within a slot 230a formed in catch/release lever 230. Depression of activation button 234 causes the compression of spring 233 which, in turn, exerts a force on hammer 229. Compression of spring 233 also causes the depression of dome switch 232. Depression of dome switch 232 initiates the flow gas through handpiece 211. Depression of dome switch 232 may also key the generator (not shown) to supply electrosurgical energy to active electrode 214. Although the flow of gas and supply of electrosurgical current may be initiated at the same time, it may be desirable to sequence the flow of gas prior to electric activation.

Complete depression of activation button 234 causes actuation button 234 to engage a catch/release lever 230. This engagement causes catch/release lever 230 to move away from hammer 229, thereby causing the release of distal end 229b of hammer 229 from within slot 230a of catch/release lever 230. The release of hammer 229 from slot 230a causes hammer 229 to strike piezoelectric crystal 228 which causes a voltage spike experienced across active electrode 214 that aids in initiation of a plasma arc. As discussed above in relation to piezoelectric device 27, piezoelectric device 227 may be used separately or in conjunction with corona start feature.

Following the initial voltage spike, piezoelectric crystal 228 may be shorted so the electrosurgical current traveling to active electrode 214 to maintain the plasma arc does not continue to pass through piezoelectric crystal 228.

The foregoing description of the embodiments of the invention has been presented for purposes of illustration and description. It is not intended to be exhaustive or to limit the invention to the precise form disclosed. Many modifications and variations are possible in light of the above teaching. The embodiments were chosen and described in order to best explain the principles of the invention and its practical application. It is to be understood that the invention can be carried out by specifically different equipment and devices, and that various modifications, both to equipment details and manufacturing methods, can be accomplished without departing from the scope of the invention itself.

What is claimed:

1. An ignition system for initiating a plasma arc in an electrosurgical system, the system comprising:
    a source of high frequency electrical energy having a terminal of active potential and a terminal of return potential;
    a base having a distal end from which a plasma arc emanates;
    an active electrode operatively coupled with the base and electrically in circuit with the terminal of active potential; and
    a piezoelectric device electrically coupled to the active electrode to create at least one high voltage spike when the system is initially activated, wherein the piezoelectric device includes a piezoelectric crystal, a striking member in the form of a cantilevered beam, and a catch lever.

2. An ignition system according to claim 1, further comprising a corona return electrode operably coupled to the base and electrically in circuit with the terminal of return potential, the corona return electrode coupled to the active electrode adjacent to the distal end of the base to form a corona discharge adjacent the distal end of the base member.

3. An ignition system according to claim 2, further comprising a dielectric member disposed between the active electrode and the corona return electrode.

4. An ignition system according to claim 1, further comprising a heater configured to preheat the active electrode prior to activation.

5. An ignition system according to claim 4 wherein the heater utilizes a current source selected from at least one of a DC current, AC current and RF current to preheat the active electrode prior to activation.

6. An ignition system according to claim 5 wherein the current source is provided by the source of high frequency electrical energy.

7. An ignition system according to claim 5 wherein the current source is provided by an independent current source.

8. An ignition system according to claim 1 further including a current sensor.

9. An ignition system according to claim 1 wherein the striking mechanism is continuously activated until a current sensor senses a current, whereupon a source of electrosurgical current maintains a normal current.

10. An ignition system according to claim 1, further including a source of ionizable gas.

11. An ignition system according to claim 10, wherein the ionizable gas is argon.

12. An ignition system according to claim 1, wherein the at least one high voltage spike is sufficient to initiate the plasma arc.

13. An ignition system according to claim 1, further including a dome switch mounted on a distal end of the cantilevered beam.

14. An ignition system according to claim 13, wherein the dome switch is configured to key gas flow and provide electrosurgical energy to the active electrode.

15. An ignition system according to claim 1, wherein the catch release includes a slot defined therein configured to selectively receive a distal end of the cantilevered beam.

* * * * *